United States Patent
Beebe

(10) Patent No.: US 9,555,213 B2
(45) Date of Patent: Jan. 31, 2017

(54) CATHETER TIP COATING SYSTEM

(71) Applicant: Fishman Corporation, Hopkinton, MA (US)

(72) Inventor: W. Scott Beebe, Berkley, MA (US)

(73) Assignee: Fishman Corporation, Hopkinton, MA (US)

( * ) Notice: Subject to any disclaimer, the term of this patent is extended or adjusted under 35 U.S.C. 154(b) by 437 days.

(21) Appl. No.: 14/145,660

(22) Filed: Dec. 31, 2013

(65) Prior Publication Data

US 2014/0190408 A1 Jul. 10, 2014

Related U.S. Application Data

(60) Provisional application No. 61/748,865, filed on Jan. 4, 2013, provisional application No. 61/881,228, filed on Sep. 23, 2013.

(51) Int. Cl.
*A61M 25/00* (2006.01)
*B05C 13/02* (2006.01)
(Continued)

(52) U.S. Cl.
CPC ............ *A61M 25/001* (2013.01); *B05C 1/027* (2013.01); *B05C 13/025* (2013.01); *A61M 25/00* (2013.01);
(Continued)

(58) Field of Classification Search
None
See application file for complete search history.

(56) References Cited

U.S. PATENT DOCUMENTS 2,674,757 A * 4/1954 Keyes, Jr. ................ B44D 3/12
15/257.075
4,655,230 A * 4/1987 Bryant .................. D06B 3/045
118/264
(Continued)

FOREIGN PATENT DOCUMENTS

CN 86101963 A 10/1986
CN 202527332 U 11/2012
(Continued)

OTHER PUBLICATIONS

Written Opinion for WO 2014/107461 (PCT/US2013/078521).*
(Continued)

*Primary Examiner* — Charles Capozzi
(74) *Attorney, Agent, or Firm* — Mark H. Whittenberger; Holland & Knight LLP

(57) ABSTRACT

A catheter tip coating assembly includes a housing defining a fluid reservoir and having a fluid outlet configured to dispense fluid to an end of a piece of tubing. The catheter tip coating assembly includes a valve assembly carried by the housing and at least partly disposed in fluid communication with the fluid reservoir. The valve assembly is configured to receive the piece of tubing and configured to move between a first position to limit fluid communication between the fluid reservoir and the fluid outlet and a second position to provide fluid communication between the fluid reservoir and the fluid outlet to dispense fluid to the end of the piece of tubing. The assembly provides for careful control over the amount of liquid that is applied and the depth of the wetting.

18 Claims, 18 Drawing Sheets

(51) Int. Cl.
B05C 1/00 (2006.01)
B05C 1/02 (2006.01)

(52) U.S. Cl.
CPC ............ *A61M 25/0009* (2013.01); *B05C 1/00* (2013.01); *B05C 1/022* (2013.01)

(56) References Cited

U.S. PATENT DOCUMENTS

| | | | | |
|---|---|---|---|---|
| 4,891,249 | A * | 1/1990 | McIntyre | B05B 7/0475 118/315 |
| 5,603,991 | A | 2/1997 | Kupiecki et al. | |
| 2009/0294472 | A1* | 12/2009 | Buckley | B05C 5/0225 222/59 |
| 2012/0301613 | A1* | 11/2012 | Doker | A61M 5/329 427/248.1 |

FOREIGN PATENT DOCUMENTS

| | | | | |
|---|---|---|---|---|
| EP | 2527042 A2 | 11/2012 | | |
| JP | 09234410 | 9/1997 | | |
| WO | WO 2014107461 A1 * | 7/2014 | ......... | A61M 25/001 |

OTHER PUBLICATIONS

Nordson EFD, "Relius UV-Cure Adhesive Coating Dispenser User Guide," pp. 1-12, 2012.
Gruppo Medica Group, "DUV Instruction Manual," pp. 1-21, 2004.
Gruppo Medica Group, "Solvent Dispensers for plastic components or tubing bonding," pp. 1-4, 2010.
Notification of the First Office Action issued in related Chinese application Serial No. 2013800695729 on Aug. 30, 2016.

* cited by examiner

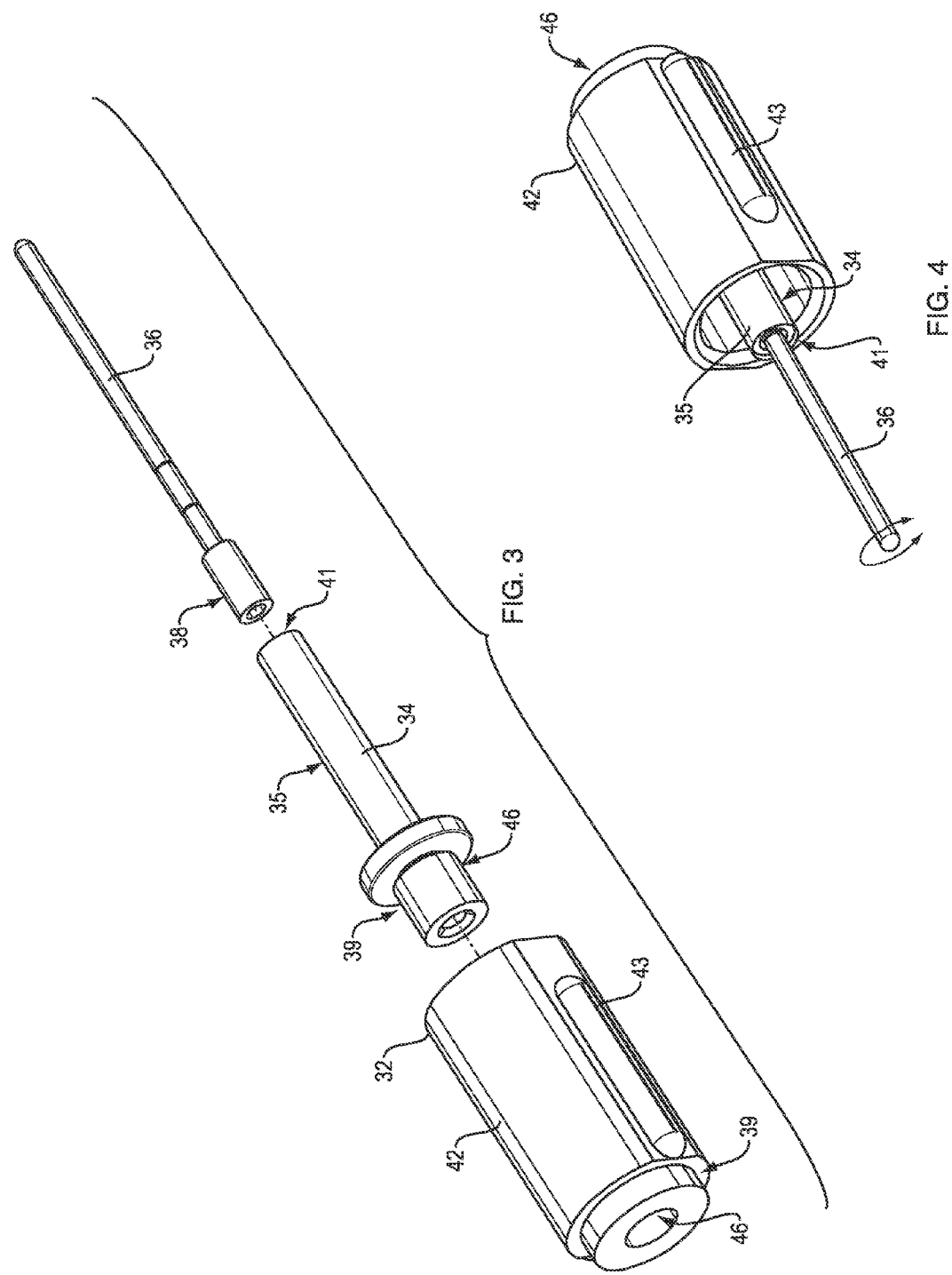

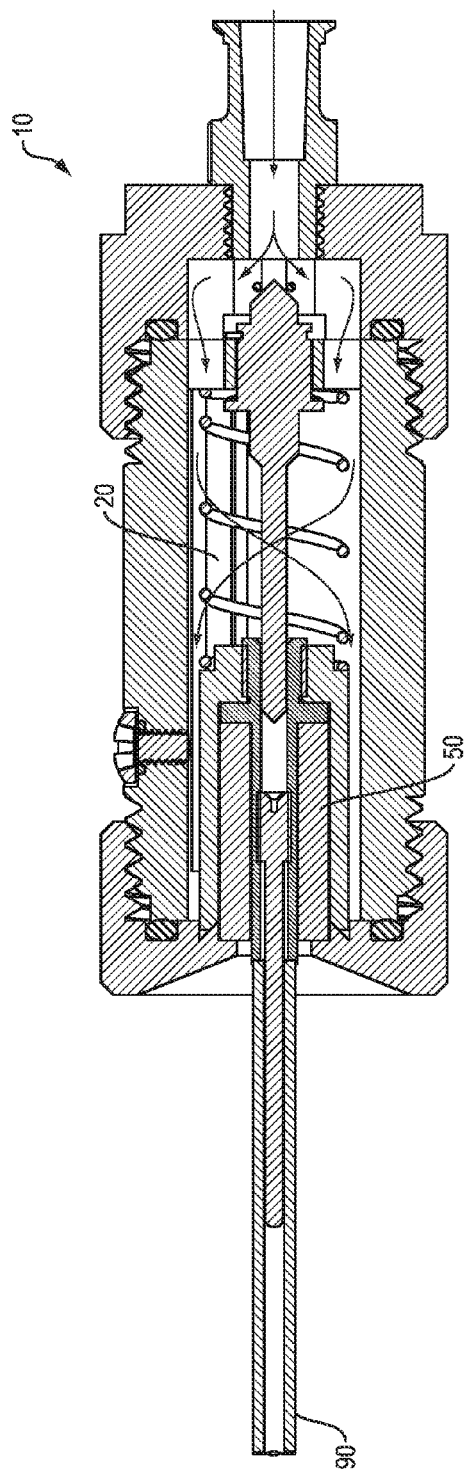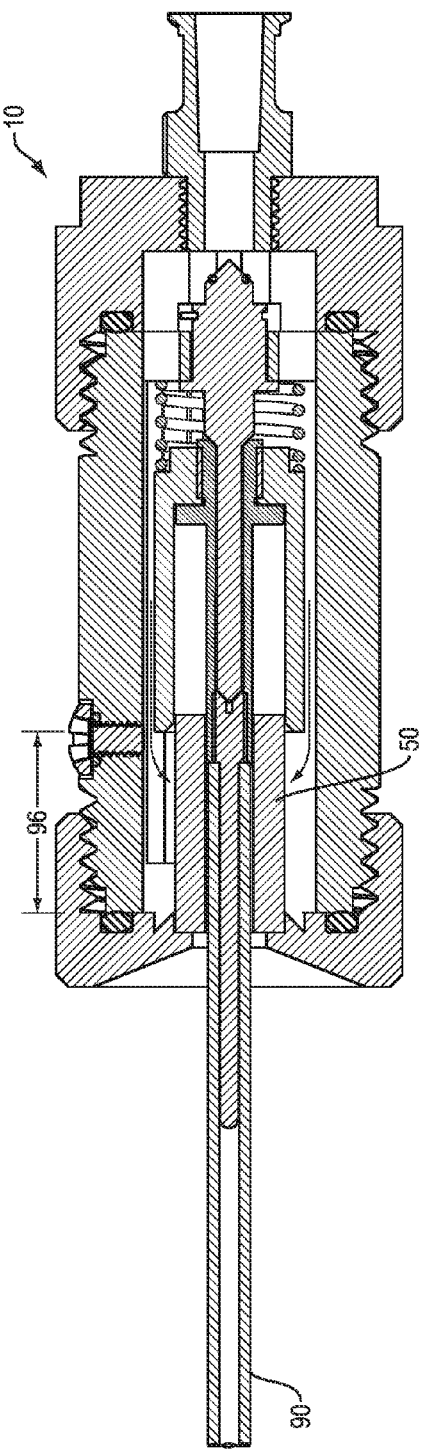

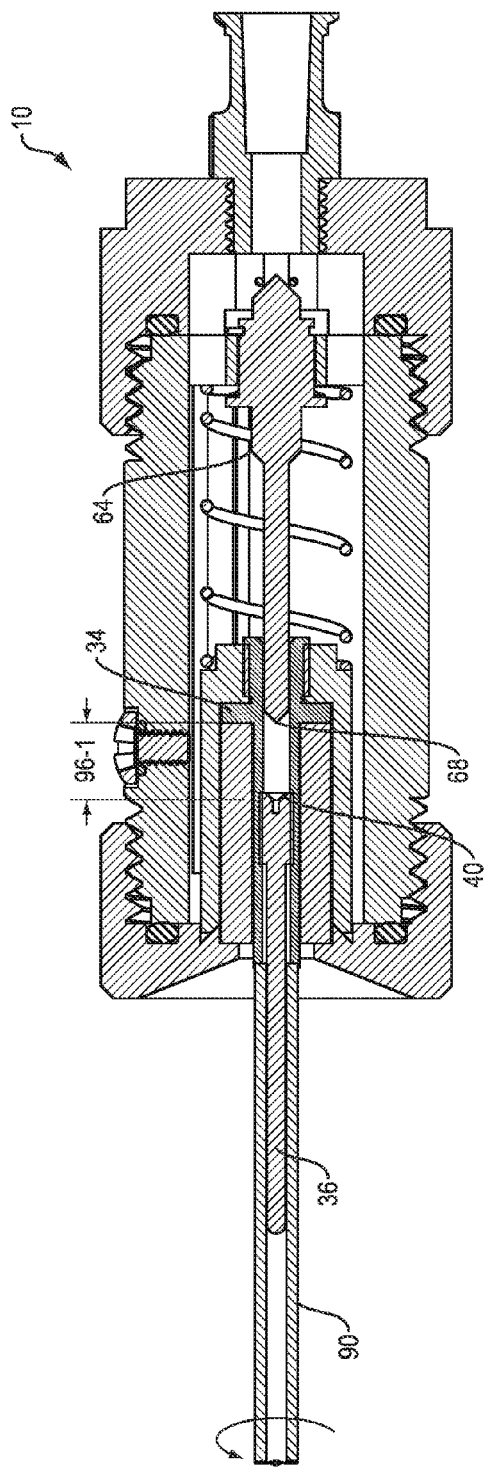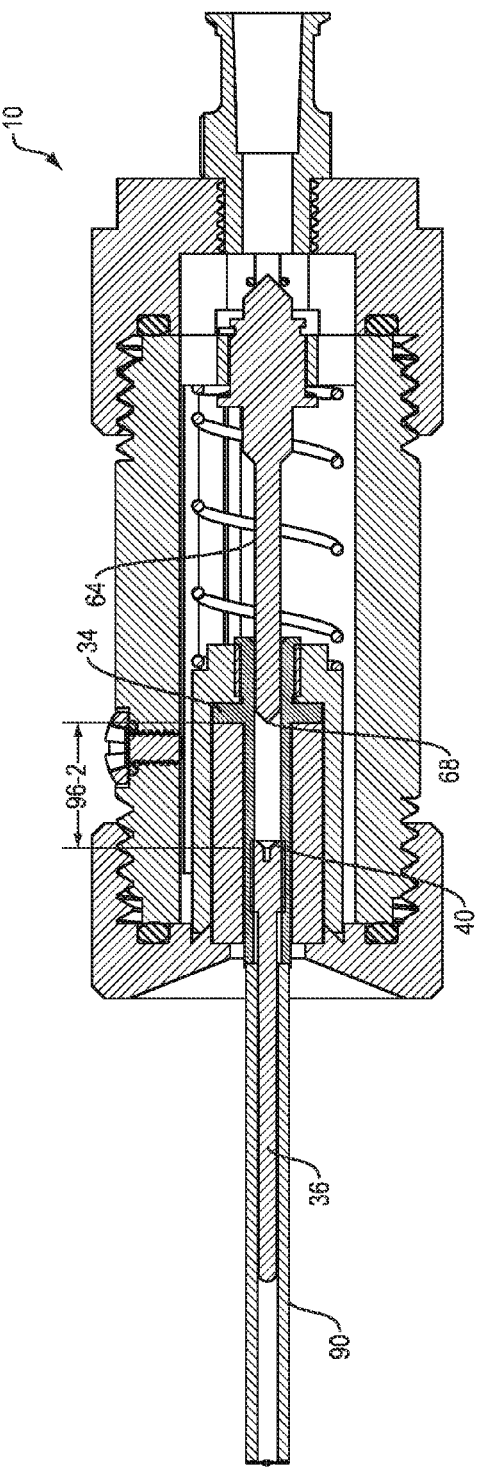

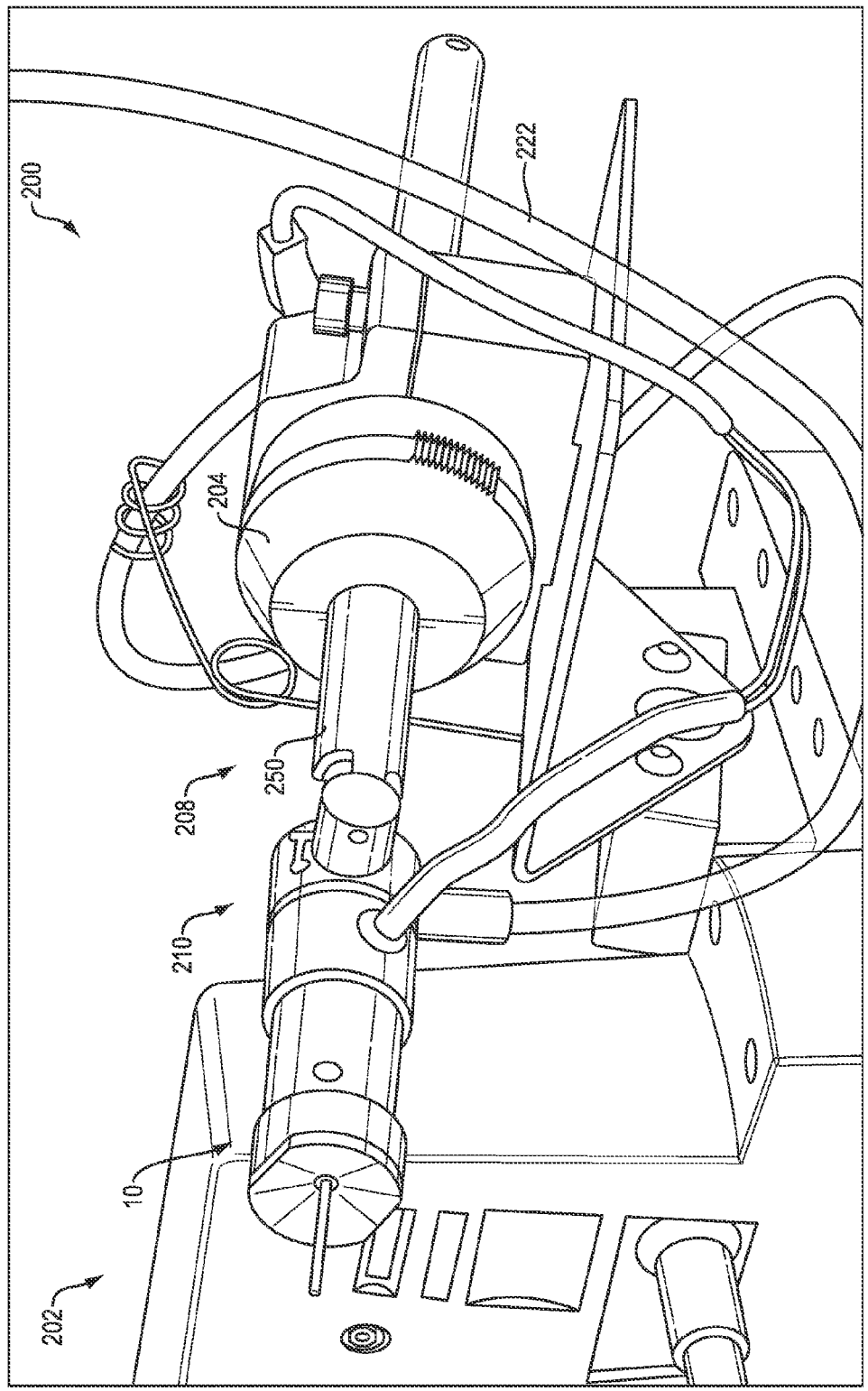

CATHETER TIP COATING SYSTEM

RELATED APPLICATIONS

This patent application claims the benefit of U.S. Provisional Application No. 61/748,865, filed on Jan. 4, 2013, entitled, "System for Selectively Wetting with a Liquid the Outside and/or Inside Surface of the End of a Length of Tubing," and of U.S. Provisional Application No. 61/881,228, filed on Sep. 23, 2013, entitled, "System for Selectively Wetting with a Liquid the Outside and/or Inside Surface of the End of a Length of Tubing," the contents and teachings of which are hereby incorporated by reference in their entirety.

BACKGROUND

Manufacturers, such as those in the medical device industry, utilize a liquid adhesive to couple tubing elements, or catheters, together. For example, the manufacturer can manually coat the outer surface one end of a first catheter with the adhesive. Next, the manufacturer can insert the end of the first catheter into a lumen of an end of a second catheter. The adhesive bonds the ends of the first and second catheters together.

SUMMARY

Conventional adhesive application techniques suffer from a variety of deficiencies. For example, application of the adhesive by hand is inexact and can lead to incomplete bonding of the ends of the catheters and leaking during use.

By contrast to conventional liquid application techniques, embodiments of the present innovation relate to a system used to controllably wet the outside and/or inside surface of an end of a length of tubing with a liquid. The system provides for careful control over the amount of liquid that is applied and the depth of the wetting. There are myriad applications of the system, one being placement of ultraviolet-activated adhesive on the end of plastic tubing that needs to be adhered to another structure. This application has usage in the medical device field such as in the attachment of a catheter tip to the catheter tube.

This disclosure features a system for selectively wetting with a liquid the outside surface of the end of tubing. The system can also be used to for selectively wet the inside surface of the tube end. One example of the system comprises a housing that contains a liquid reservoir that has a liquid outlet, and a valve that selectively allows for liquid flow through the liquid outlet, where the valve assembly is opened so as to allow for fluid flow by insertion of the end of the tubing into the housing, and the valve closes automatically when the tubing is withdrawn from the housing. The system typically also has a pump that supplies fluid to the reservoir, with a switch carried in the housing that operates the pump. There can be a switch actuator that opens and closes the switch, where the switch actuator is indirectly moved by the tubing. The indirect movement of the switch actuator may be provided by a plunger tip that is adapted to be contacted by the end of the tubing, and may further be by a plunger core that adjustably receives the plunger tip.

The system also preferably allows for adjustment of the length of the wetted end of the tubing, which can be accomplished with the plunger tip that is adapted to be contacted by the end of the tubing, and where the plunger core adjustably, threadably receives the plunger tip. The system preferably employs a porous material at the liquid outlet, where the valve assembly is movable between a closed position in which it blocks fluid from moving from the reservoir to the porous material, to an open position in which it allows for a defined volume of fluid flow from the reservoir to the porous material, and hence onto the outside end of the tubing.

In one arrangement, a catheter tip coating assembly includes a housing defining a fluid reservoir and having a fluid outlet configured to dispense fluid to an end of a piece of tubing. The catheter tip coating assembly includes a valve assembly carried by the housing and at least partly disposed in fluid communication with the fluid reservoir. The valve assembly is configured to receive the piece of tubing and configured to move between a first position to limit fluid communication between the fluid reservoir and the fluid outlet and a second position to provide fluid communication between the fluid reservoir and the fluid outlet to dispense fluid to the end of the piece of tubing. The system provides for careful control over the amount of liquid that is applied and the depth of the wetting.

In one arrangement, a fluid application system includes a controller disposed in electrical communication with a motor apparatus, the controller and motor apparatus configured to control an amount of fluid provided to a catheter tip coating assembly. The catheter tip coating assembly includes a housing defining a fluid reservoir and having a fluid outlet configured to dispense fluid to an end of a piece of tubing. The catheter tip coating assembly includes a valve assembly carried by the housing and at least partly disposed in fluid communication with the fluid reservoir. The valve assembly is configured to receive the piece of tubing and configured to move between a first position to limit fluid communication between the fluid reservoir and the fluid outlet and a second position to provide fluid communication between the fluid reservoir and the fluid outlet to dispense fluid to the end of the piece of tubing. The system includes a stopcock assembly configured to selectively couple a fluid reservoir with the catheter tip coating assembly and with a metering cylinder, the metering cylinder disposed in operational communication with the motor apparatus.

BRIEF DESCRIPTION OF THE DRAWINGS

The foregoing and other objects, features and advantages will be apparent from the following description of particular embodiments of the innovation, as illustrated in the accompanying drawings in which like reference characters refer to the same parts throughout the different views. The drawings are not necessarily to scale, emphasis instead being placed upon illustrating the principles of various embodiments of the innovation.

FIG. 3 is an exploded view of the plunger tip, plunger core, and plunger, in one arrangement.

FIG. 4 is an assembled view of the plunger tip, plunger core, and plunger, in one arrangement.

6A illustrates a fluid flow path for the dispensing system when the valve assembly is disposed in a closed position.

FIG. 6B illustrates a fluid flow path for the dispensing system when the valve assembly is disposed in an opened position.

FIG. 7A illustrates a first variable depth setting of the dispensing system for wetting the tubing.

FIG. 7B illustrates a first variable depth setting of the dispensing system for wetting the tubing.

Figure 8:
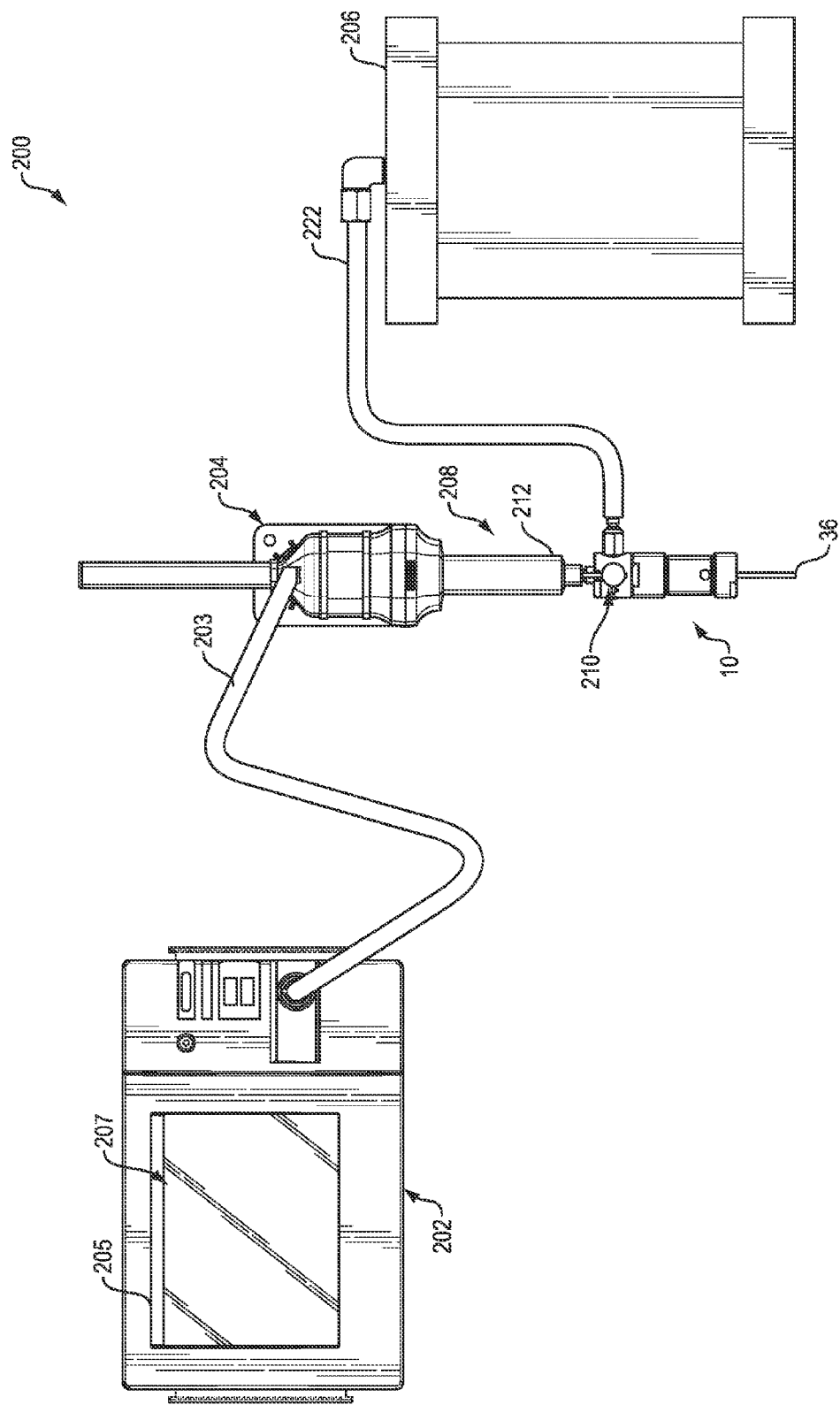

FIG. 8 illustrates a schematic representation of a fluid application system, according to one arrangement.

FIG. 9 illustrates a dispensing system and motor apparatus of the fluid application system of FIG. 8.

Figure 10A:
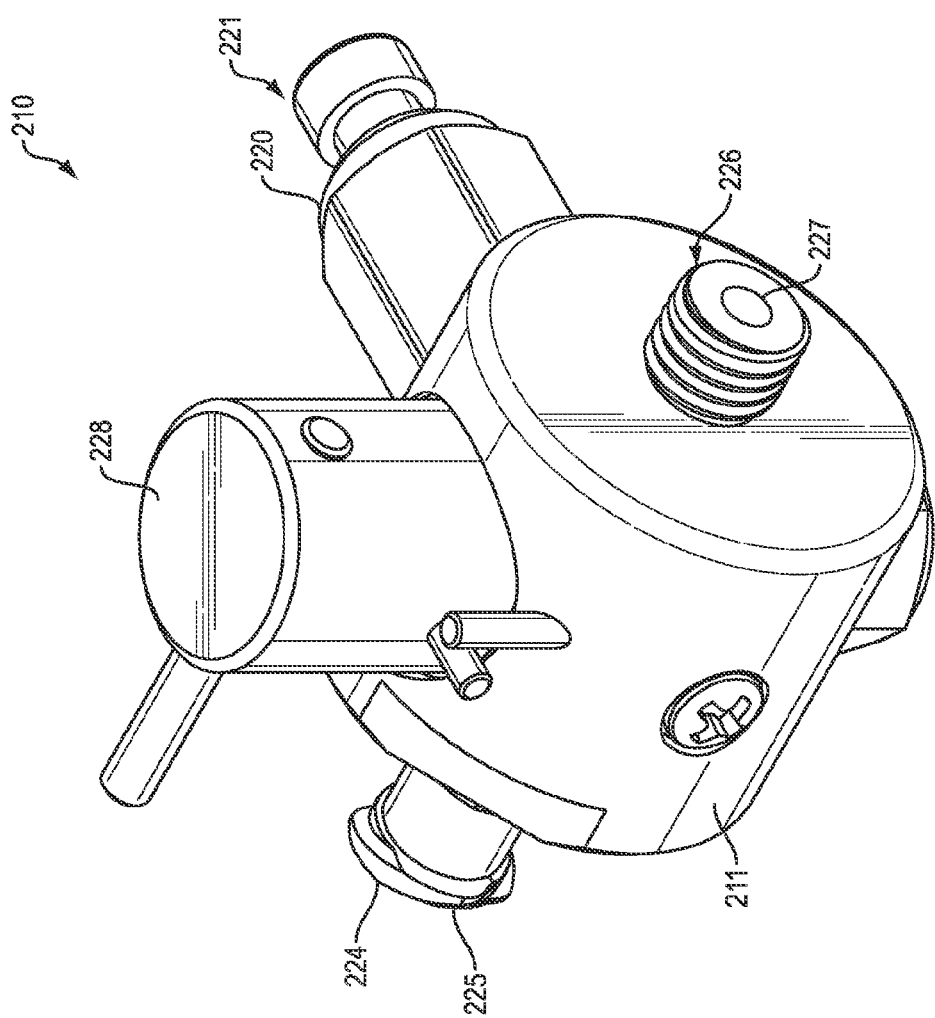

FIG. 10A illustrates a front perspective view of an arrangement of a stopcock assembly of the application system of FIG. 8.

FIG. 10 B illustrates a rear perspective view of the arrangement of the stopcock assembly of the application system of FIG. 8.

Figure 10B:
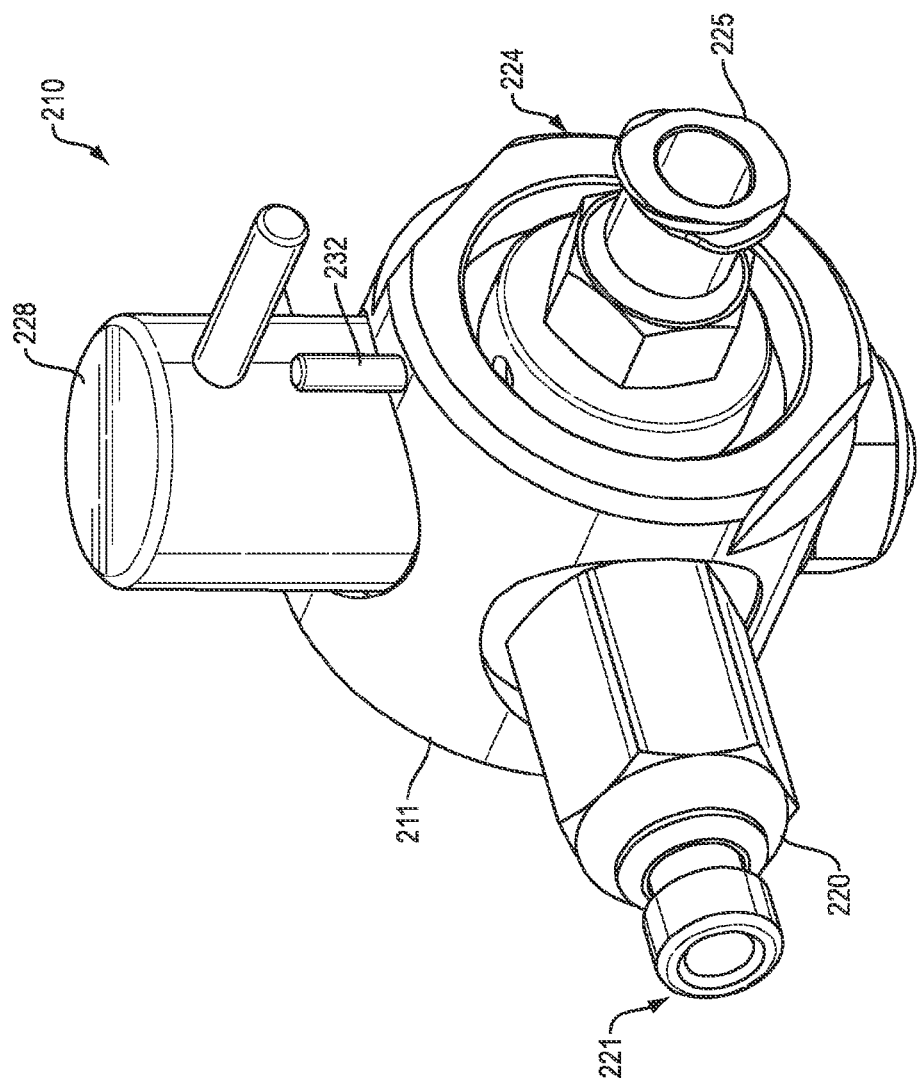
Figure 10C:
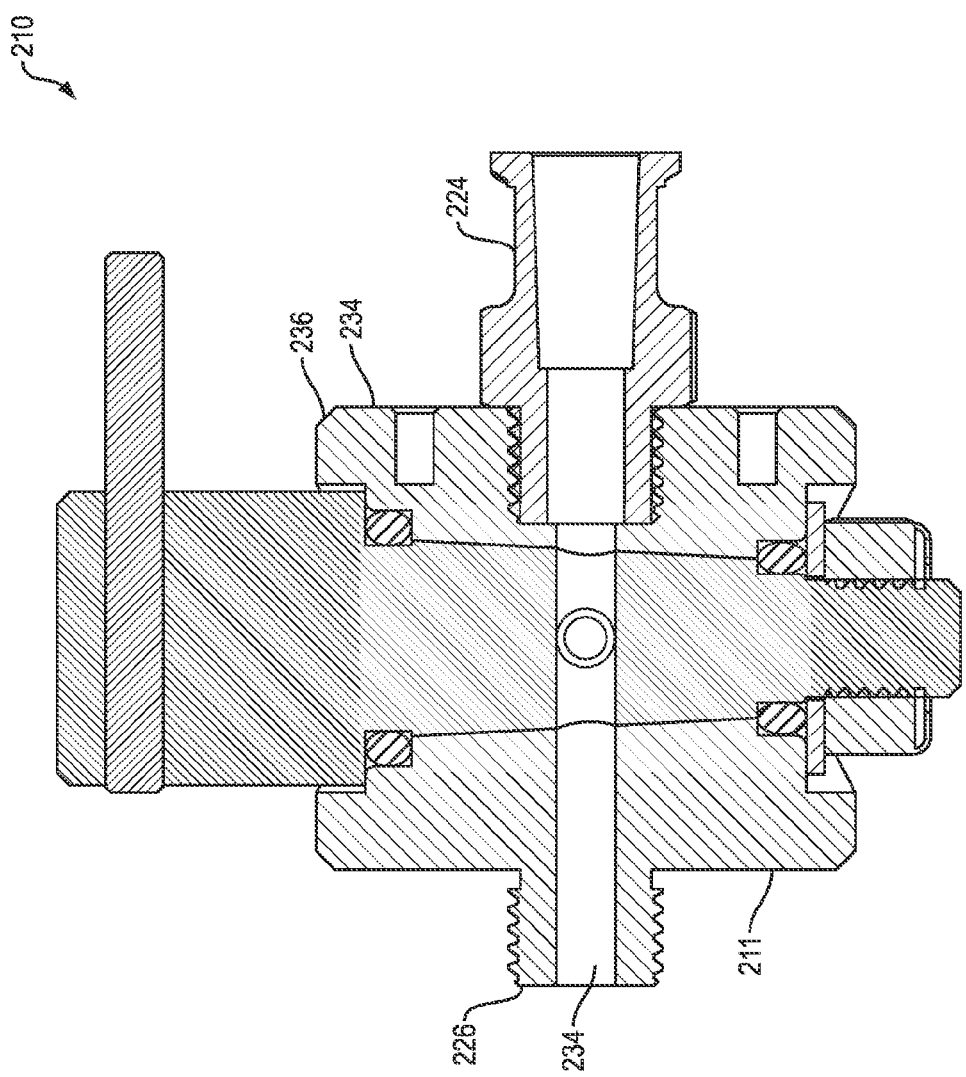

FIG. 10C illustrates a side sectional view of the stopcock assembly of the application system of FIG. 8.

Figure 11:
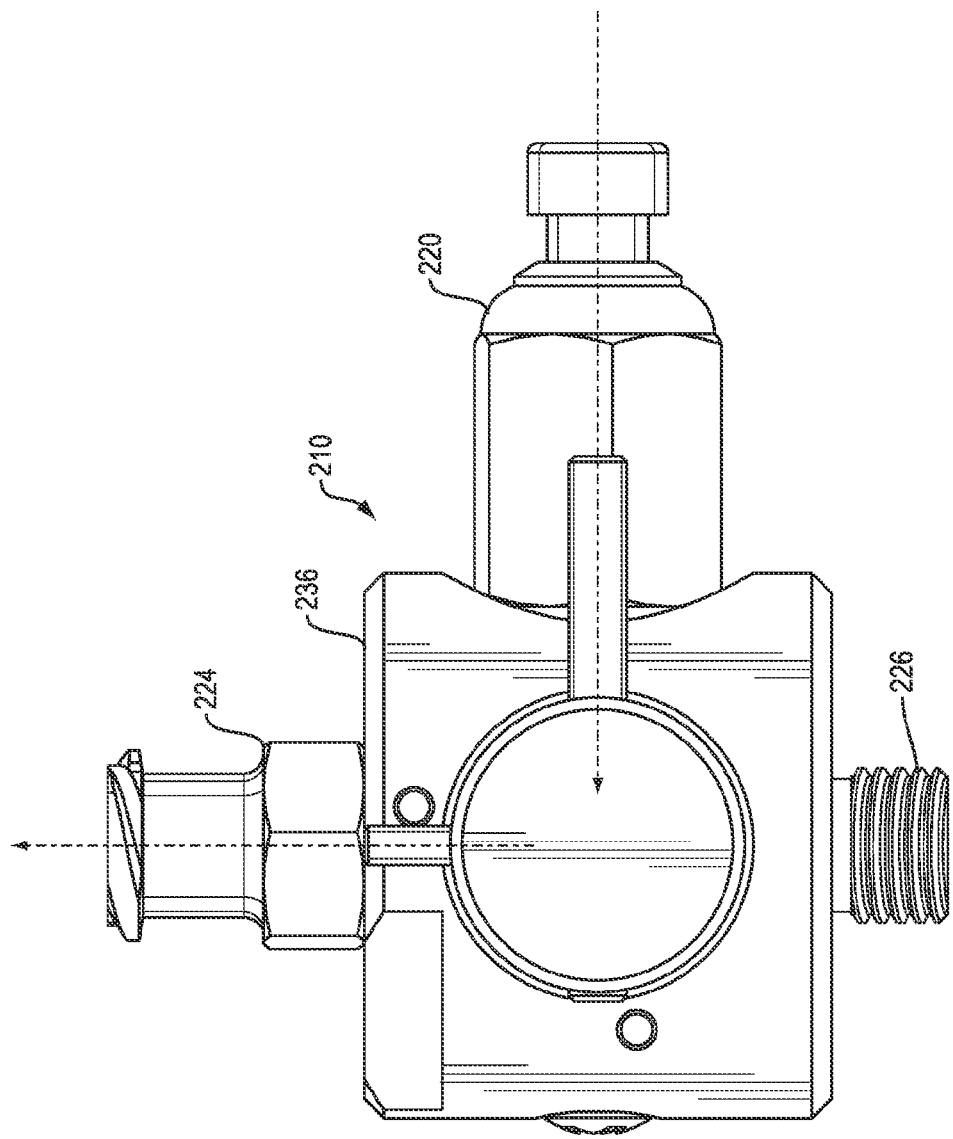

FIG. 11 illustrates the stopcock assembly of FIGS. 10A through 10C having a stopcock barrel disposed in a first rotational position.

Figure 12:
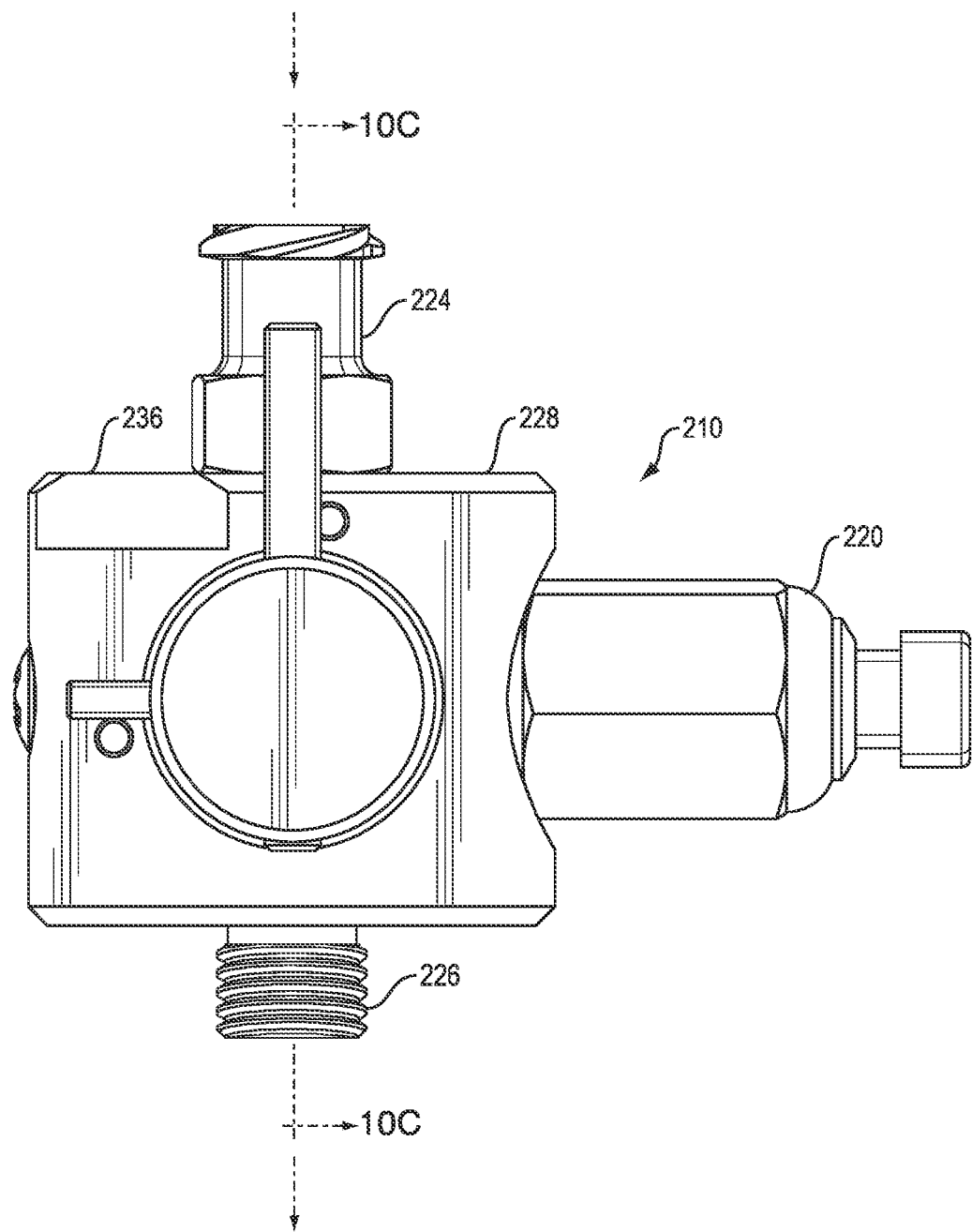

FIG. 12 illustrates the stopcock assembly of FIGS. 10A through 10C having a stopcock barrel disposed in a second rotational position.

Figure 13:
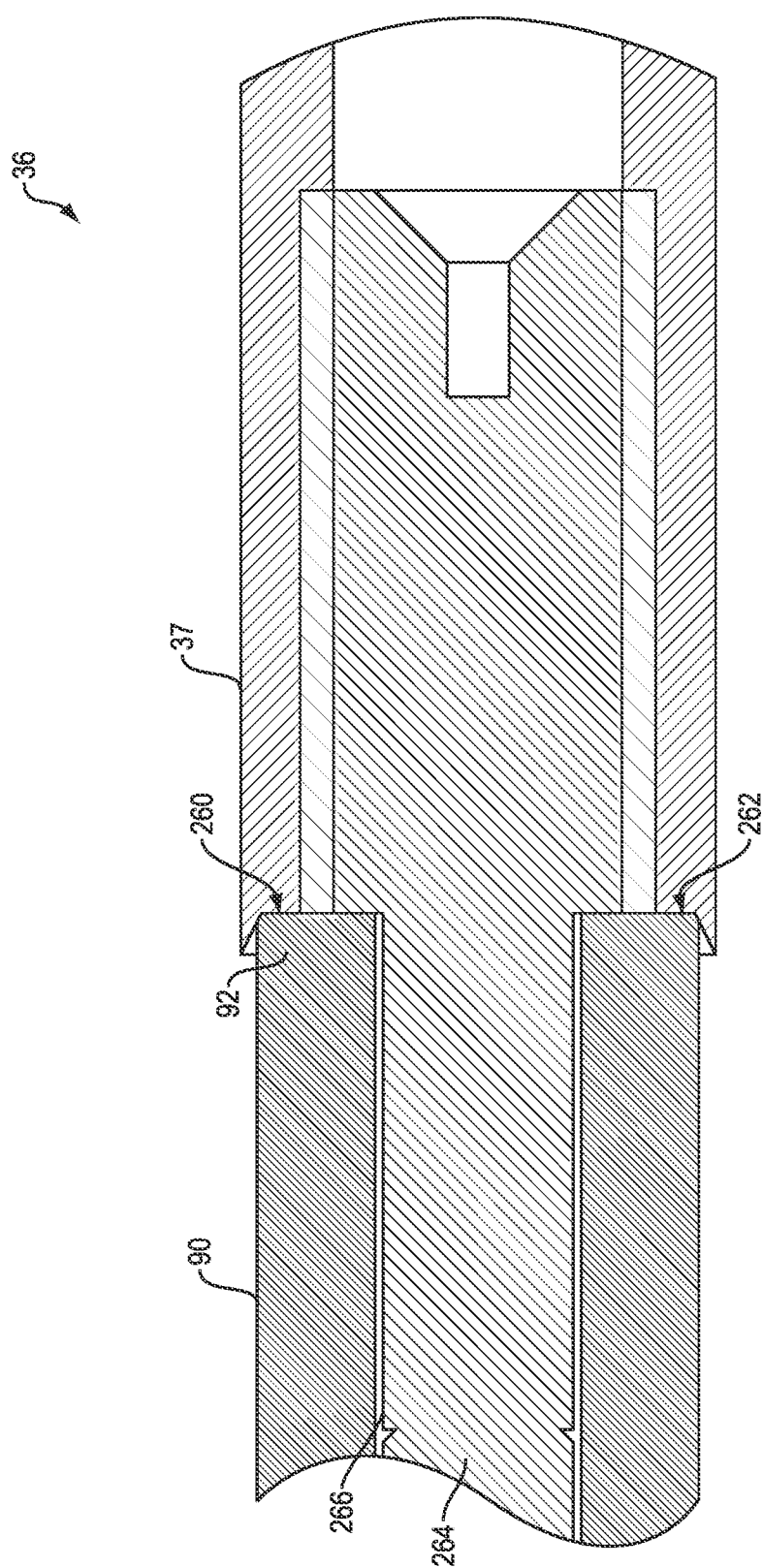

FIG. 13 illustrates an arrangement of a plunger tip.

Figure 14:
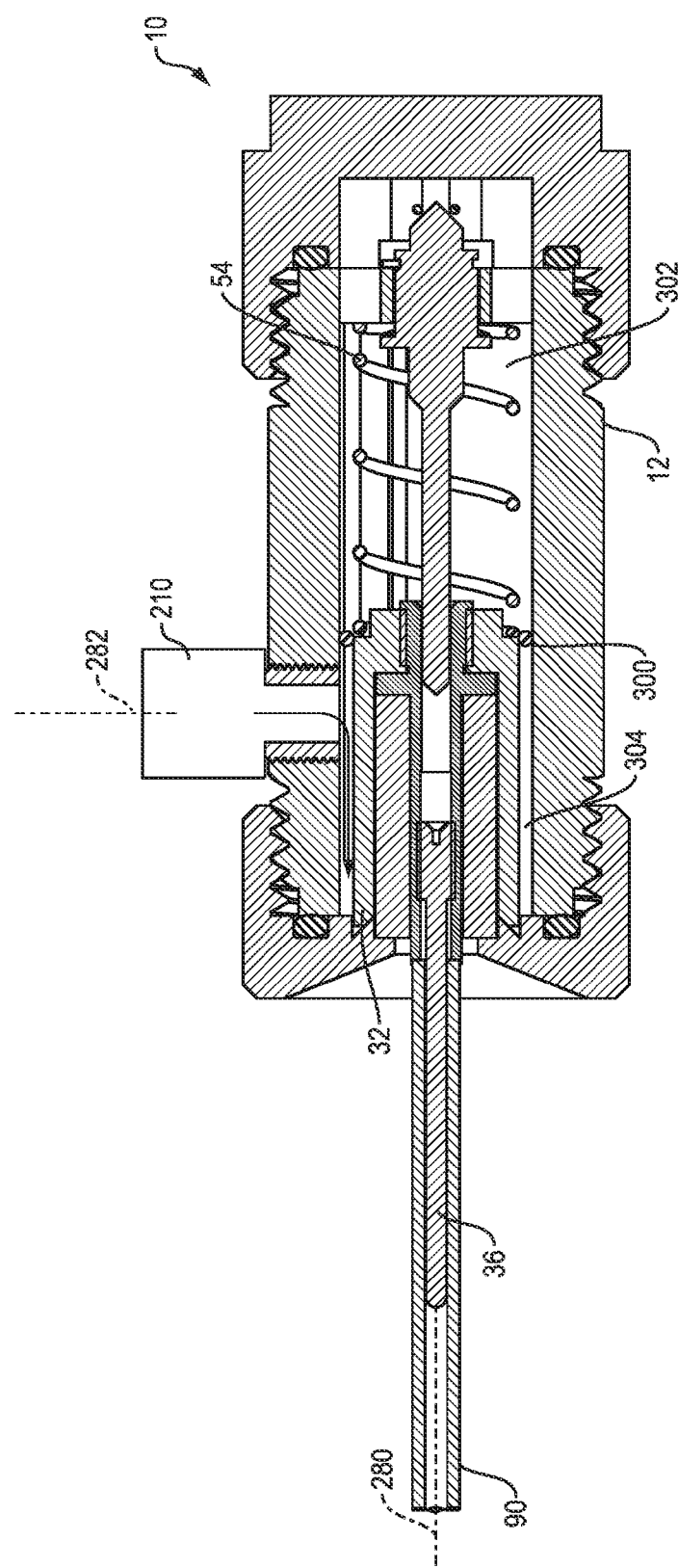

FIG. 14 illustrates a sectional view of a dispensing system, according to one arrangement.

Figure 15:
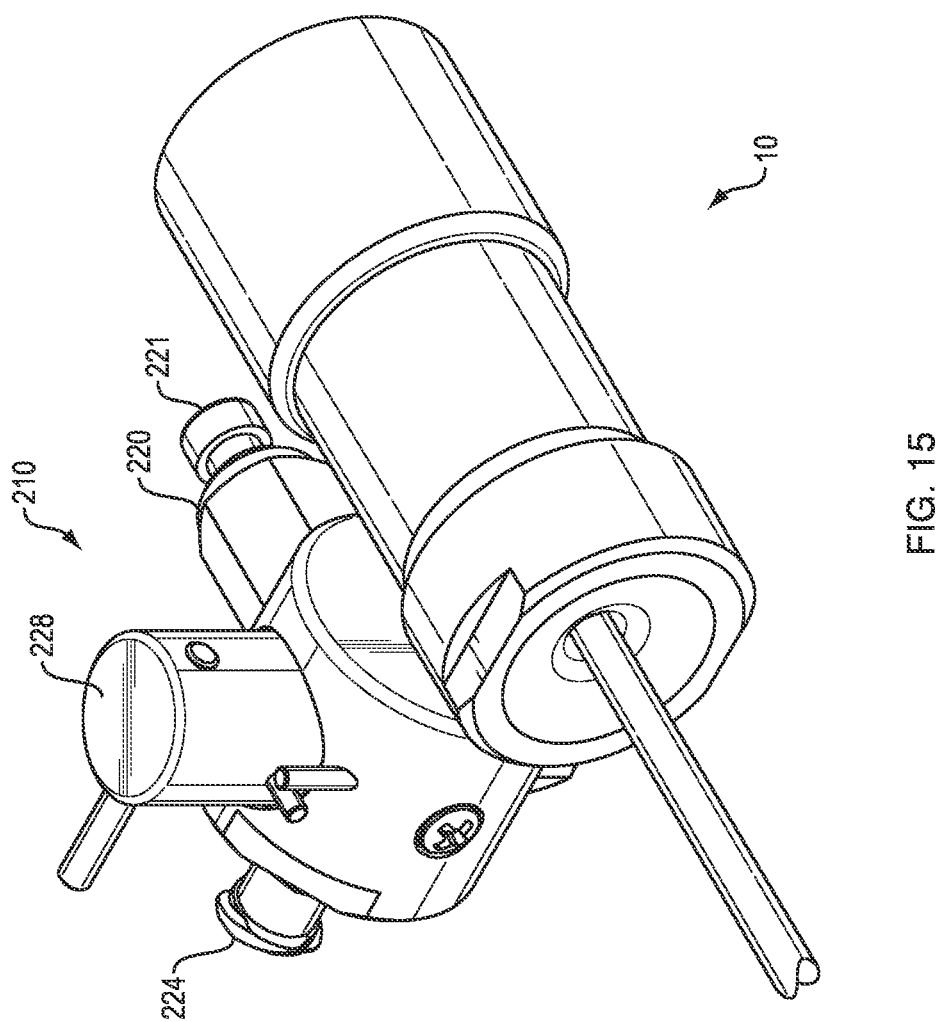

FIG. 15 illustrates a perspective view of the dispensing system of FIG. 14, according to one arrangement.

DETAILED DESCRIPTION

Figure 1:
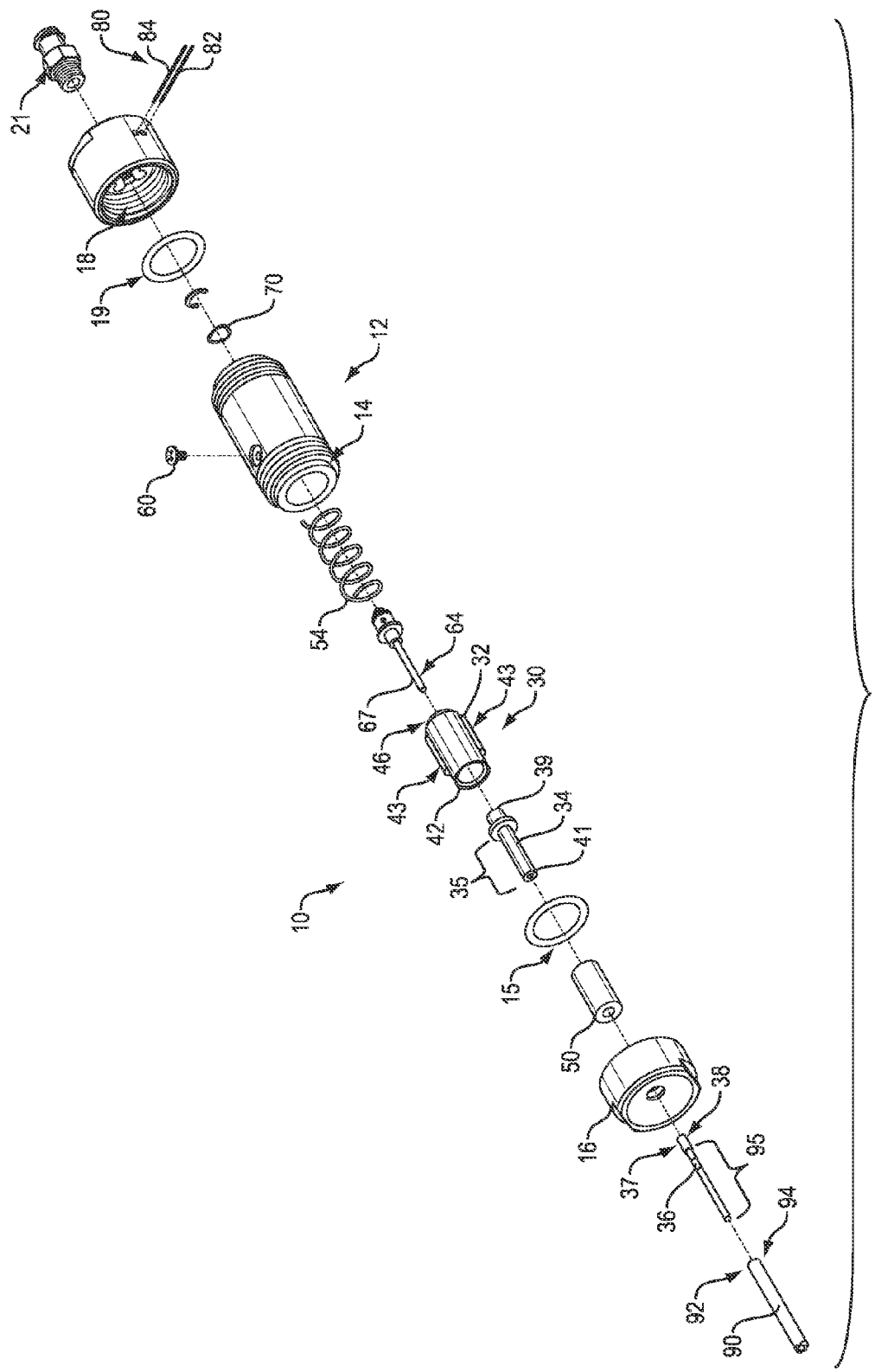
FIG. 1 illustrates an exploded view of a dispensing system, according to one arrangement.
Figure 2A:
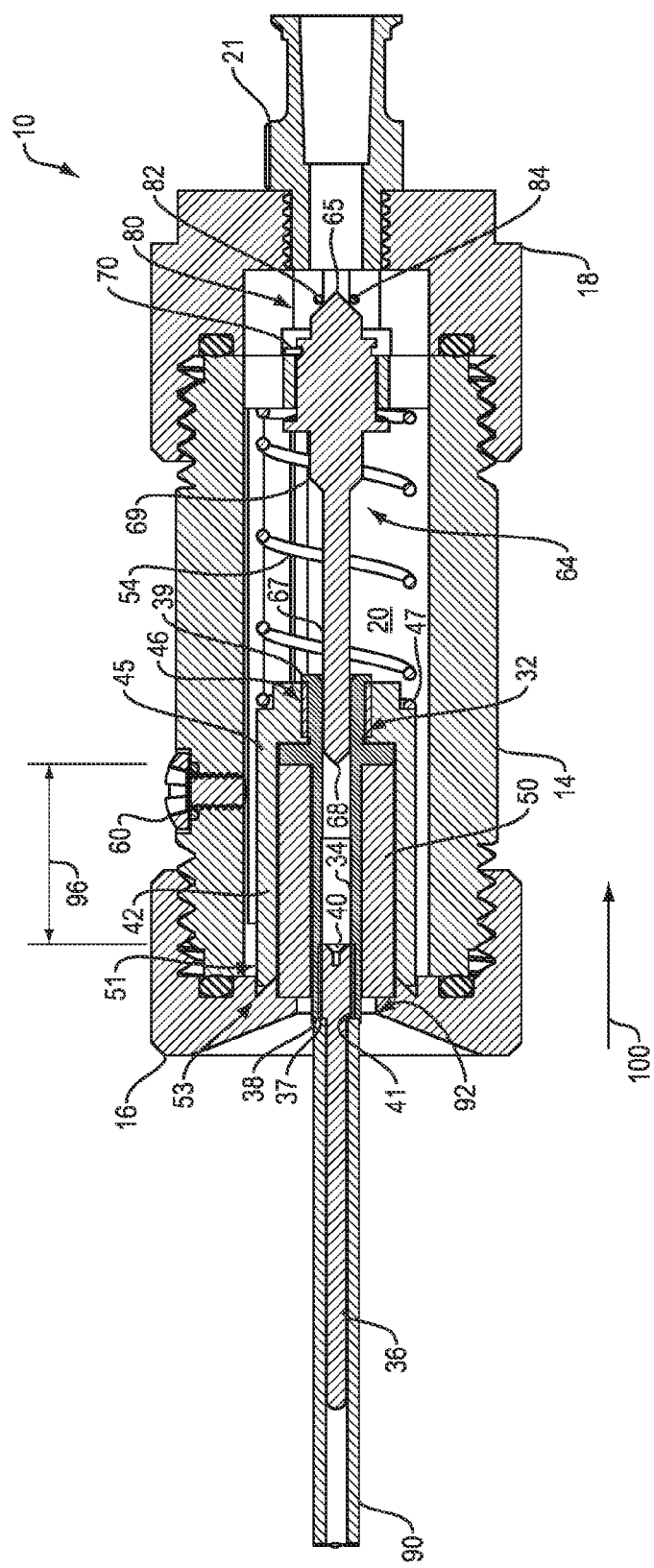
FIG. 2A illustrates the system of FIG. 1 having a valve assembly disposed in a closed position.
Figure 2B:
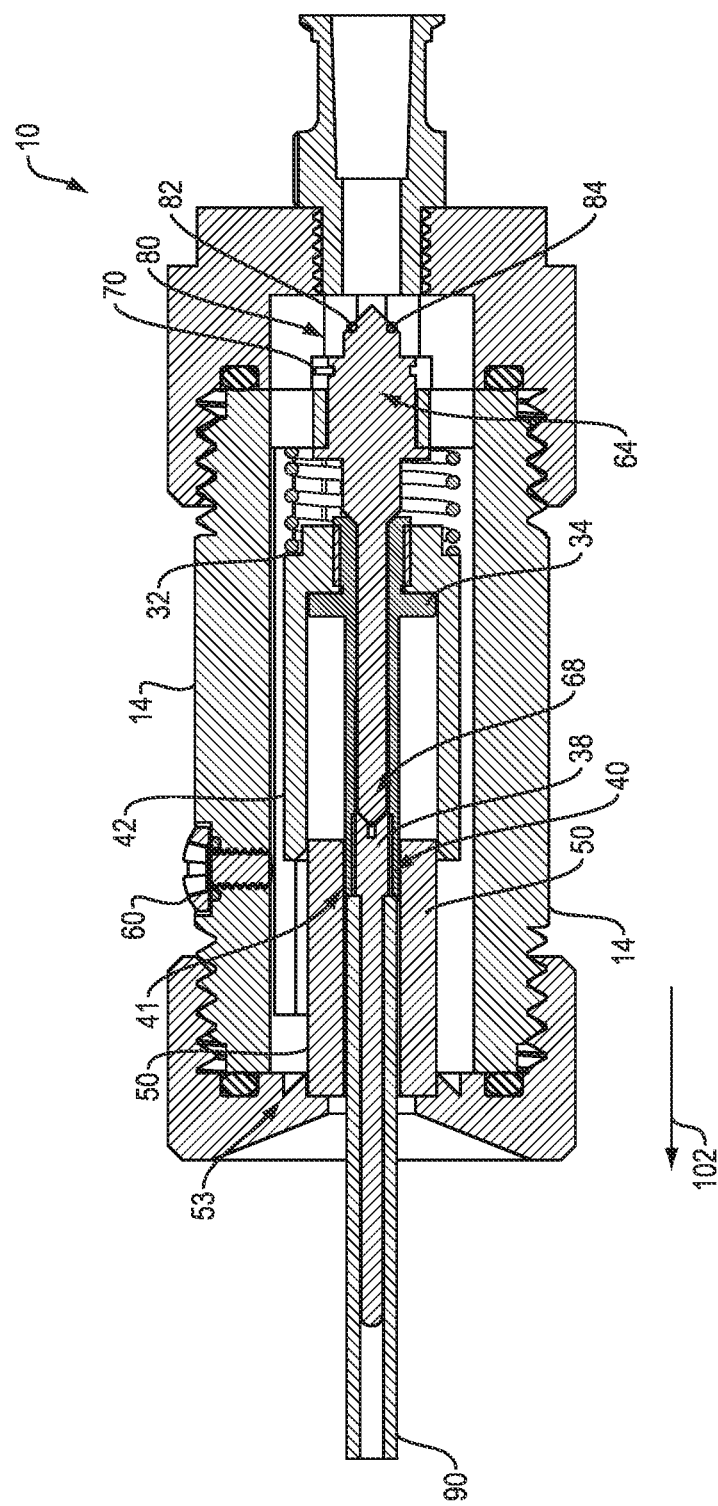
FIG. 2B shows the system of FIG. 1 with the valve assembly disposed in an open position and the tubing pushed in and being wetted.
Figure 2C:
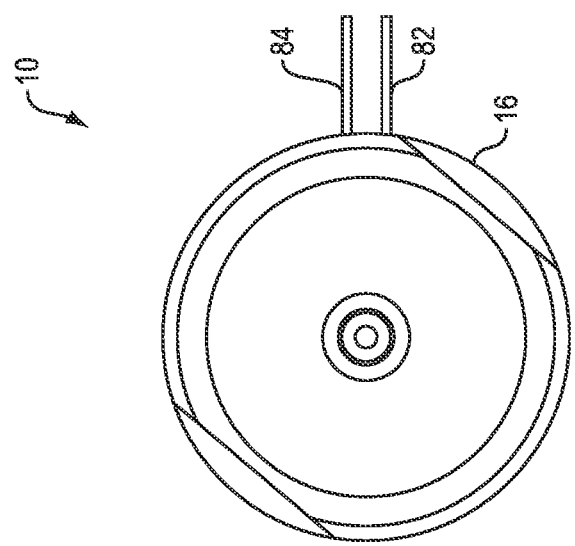
FIG. 2C is an end view of the system of FIG. 1.

FIGS. 1-2C illustrate an example of a dispensing system 10, termed a catheter tip coating assembly herein. As will be described below, the catheter tip coating system 10 is configured to dispense a volume of a fluid, such as a liquid adhesive, onto an end portion of a piece of tubing 90, such as a catheter. In one arrangement, the catheter tip coating system 10 includes a housing 12 and a valve assembly 30 at least partially carried by the housing 12.

The housing 12 is configured to contain the fluid to be applied to an outside area 94 of an end 92 of the tubing 90 that is inserted into the housing 12. For example, the housing 12 includes a barrel 14, a first seal 15 and first end cap 16 coupled to a first end of the barrel 14, and a second seal 19 and a second end cap 18 coupled to a second end of the barrel 14. The housing 12 defines an open volume or reservoir 20 configured to contain the fluid for distribution to the tubing 90 via a fluid outlet. While the reservoir 20 can receive the fluid from a variety of sources, in one arrangement, the housing 12 includes a luer fitting 21 configured to be coupled to a fluid source (not shown) or to a stopcock assembly 210, as will be described below.

In one arrangement, the fluid outlet of the housing 12 is selectively disposed between the reservoir 20 and the tubing 90 by the valve assembly 30. For example, the fluid outlet can be configured as a porous tube 50 disposed at the first end of the barrel 14. The porous tube 50 can be configured in a variety of ways. For example, the porous tube 50 can be manufactured from a cylindrical, or tubular, porous material, such as POREX. In another example, the porous tube 50 can be manufactured as a cylindrical structure, such as formed from a metallic material (e.g., stainless steel), that defines a set of openings extending through the wall of the cylindrical structure. The porous tube 50 defines a bore and has an internal diameter that almost matches the outside diameter of the tubing 90 so that the tubing 90 is located very close to (e.g., about 0.002 inches from) porous tube 50. With such an arrangement, and in operation, the porous tube is configured to 50 transfer fluid from the reservoir 20 and onto tube area 94.

The valve assembly 30 carried by the housing 12 is configured to be disposed between a first, closed position, as shown in FIG. 2A, and a second, opened position, as shown in FIG. 2B when the tubing 90 is pushed into the housing 12. With such a configuration, the valve assembly 30 selectively uncovers the porous tube 50 to allow fluid in the reservoir 20 to reach tubing area 94.

The valve assembly 30 can be configured in a variety of ways. In one arrangement, the valve assembly 30 includes plunger 32, plunger core 34, and plunger tip 36.

Figure 5:
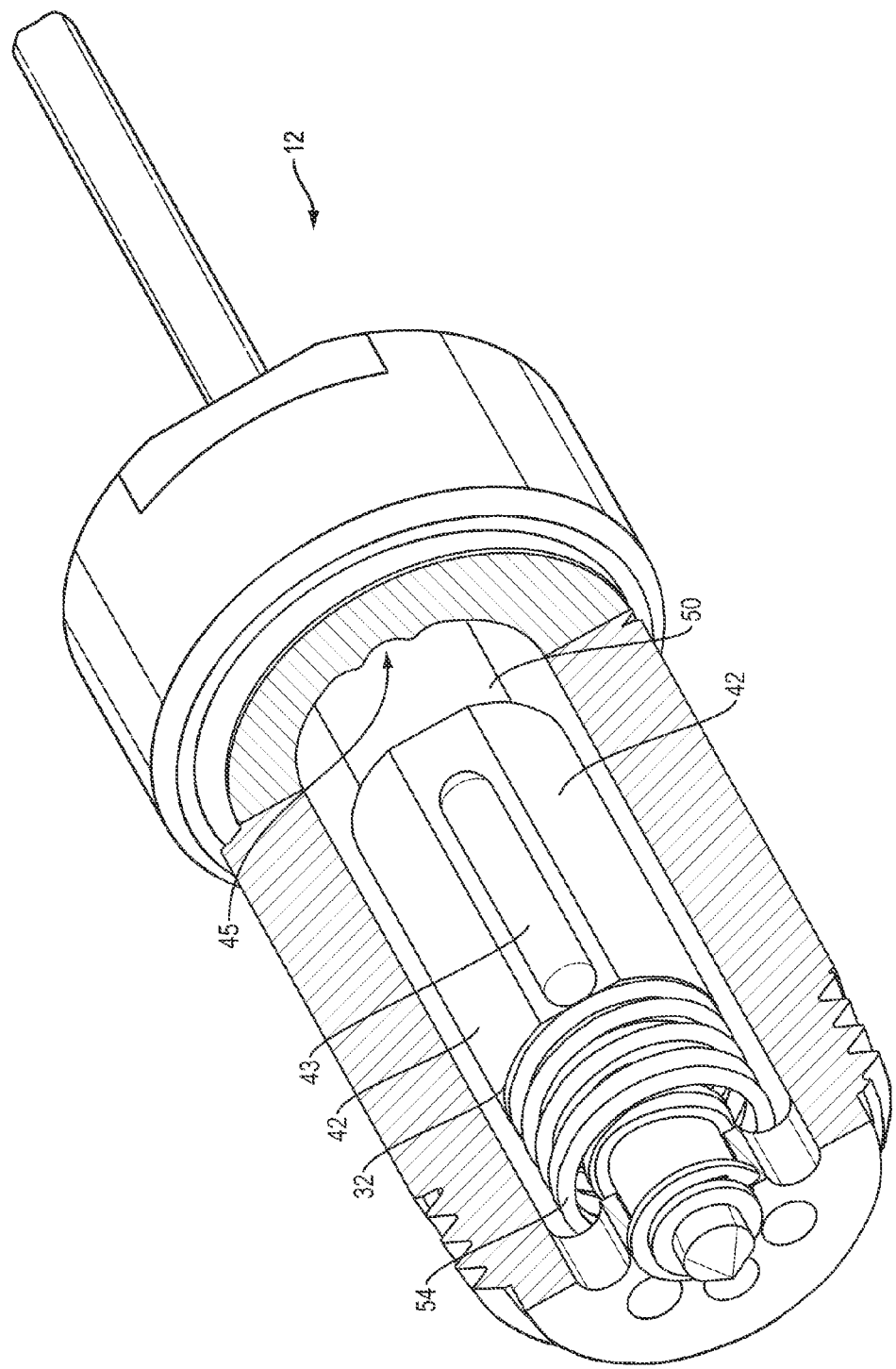
FIG. 5 is a perspective, partially cross-sectional view of the plunger and the barrel.

The plunger tip 36 is configured as an elongate structure configured to receive the tubing 90. For example, the plunger tip 36 includes a shaft portion 95 and a shoulder element 97. In use, a length of the tubing 90 is disposed on the shaft portion 95 and an end 92 of the tubing 90 is disposed against the shoulder element 37 of the plunger tip 36. As best shown in FIGS. 4 and 5, a threaded end portion 38 of the plunger tip 36 is received by an internally threaded end 41 of the plunger core 34. The depth of the threaded interface between end portion 38 the plunger tip 36 and threaded end 41 of the plunger core 34 is adjustable, to adjust the length 34 of the tubing 90 that is coated with fluid, as explained below.

The plunger core 34 is configured to couple the plunger tip 36 to the plunger 32. For example, with continued reference to FIGS. 4 and 5, the opposing or second end 39 of the plunger core 34 can be threaded into an end 46 of the plunger 32. Accordingly, during operation, the plunger 32, plunger core 34, and plunger tip 36 of the plunger assembly 30 translate in unison within the barrel 14 along a longitudinal axis between the first end cap 16 and a second end cap 18.

In one arrangement, the plunger core 34 is slidably disposed within an inner diameter of the porous tube 50. For example, the plunger core 34 includes a shaft 35 extending between the threaded end 41 and the opposing end 39. The shaft 35 is configured to translate relative to the porous tube 50 when the valve assembly 30 is moved between the first position (FIG. 2A) and the second position (FIG. 2B). Accordingly, when disposed in the first position, the plunger core 34 limits fluid communication between the porous tube 50 and the tubing 90 and when disposed in the second position, the plunger core 34 allows fluid communication between the porous tube 50 and the tubing 90.

Plunger 32 has body portion 42 that defines a substantially cylindrical wall structure, as illustrated in FIGS. 3 through 5. Additionally, the body portion 42 has a pair of opposing ribs 43 extending along its length. As best illustrated in FIGS. 2A and 2B, the body portion 42 is disposed between an inner wall of the barrel 14 and an outer portion of the porous tube 50. As further illustrated in FIG. 5, the pair of ribs 43 insert within corresponding channels 45 defined by the inner wall of the barrel 14. With such an arrangement, the inner wall of the barrel 14 and the outer portion of the porous tube 50 guides the plunger 32, and minimizes axial rotation of the plunger 32, as it translates along a longitudinal axis relative to the barrel 14.

The plunger 32 is configured to selectively limit or allow fluid communication between the porous tube 50 and the reservoir 20. For example, the body portion 42 is configured to operate as a valve to selectively provide a fluid path from the reservoir 20 to the outside of porous tube 50, as indicated in FIGS. 2A and 2B. With continued reference to FIG. 2A, in one arrangement, when the plunger 32 is disposed in a first or closed position relative to the barrel 14, a first end 51 of the body portion 42 is disposed within a channel 53 defined by a first end cap 16 of the catheter tip coating assembly 10. Such positioning minimizes leakage of fluid within the reservoir 20 to a location external to the catheter tip coating assembly 10.

During operation, a spring 54 holds the valve assembly 30 in a normally closed position (i.e., with the valve closed) shown in FIG. 2A, where the body portion 42 closes fluid access to the porous tube 50. When tubing end 92 is pushed into the housing 12, the tubing 90 generates a load on the valve assembly 30 and causes the valve assembly 30 to translate along direction 100. This, in turn, translates the body portion 42 of the plunger 32 along direction 100 to expose the outer diameter of the porous tube 50 to the fluid reservoir 20 and translates the plunger core 34 along direction 100 to provide fluid communication between the porous tube 50 and the tubing 90, as illustrated in FIGS. 2A and 2B. Such positioning of the valve assembly 30 from the closed to the open position, as indicated in FIGS. 6A and 6B, allows for fluid flow from the reservoir 20 to porous tube 50, and, in turn, onto the tubing portion 94. With reference to FIGS. 2A and 2B, movement of the valve assembly 30 is stopped when a cavity 40 at the interior end of plunger tip 36 contacts a stop tip 68 of a switch actuator 64 and the switch actuator 64 translates along direction 100 against a switch actuator return spring (e.g., a Belleville washer) 70.

With reference to FIG. 2B, when the tubing 90 is withdrawn from housing 12, the spring 70 pushes the switch actuator 64 along a direction 102, and the spring 54 pushes the plunger assembly 30 along the direction 102 back to the closed position, as shown in FIG. 2A. This action closes the valve assembly 30 so that leakage of fluid and/or fluid fumes from the reservoir 20 is minimized or prevented. With such positioning, the catheter tip coating assembly 10 is ready for the next coating action.

Accordingly, the catheter tip coating assembly 10 is configured to controllably wet an end of a length of tubing 90 with a fluid, such as a liquid adhesive. The system 10 provides for careful control over the amount of fluid that is applied to the tubing 90, as well as to the depth of the wetting.

In one arrangement, catheter tip coating assembly 10 is configured to generate a control signal in response to motion of the valve assembly 30. As indicated above, the opposing end 39 of plunger core 34 fits over, and is guided by, a guide end portion 67 of an electrically conductive switch actuator 64. An end of the switch actuator 64, in one arrangement, is enlarged and shaped as a cone 65 so that it intermittently closes a switch 80 by contacting spaced switch contacts 82 and 84.

For example, with reference to FIGS. 2A and 2B, in response to translation of the valve assembly 30 along direction 100, the conical tip 65 of the switch actuator 64 translates along direction 100 until it touches both of the spaced switch contacts 82 and 84 to close the switch 80. In one arrangement, the displacement of the switch 80 in and open and close motion along direction 100 is about 0.010 inches. Closing switch 80 in this manner sends a signal to a liquid pump (not shown), which then pumps a predefined volume of fluid into reservoir 20, or to a controller (described below), which is configured to control the pumping of a predefined volume of fluid into reservoir 20. This action provides both the liquid volume and pressure to supply a predefined amount of fluid to porous tube 50 and push the fluid through the tube onto area 94 of tubing 90 that is in contact with or lies very close to the ID of porous tube 50, thus coating the tubing end 94 with the fluid. While the switch actuator 64 is illustrated and described as including a conical tip 65 configured to selectively touch contacts 82, 84, the switch actuator 64 and contacts 82, 84 can be configured in a variety of ways to selectively signal the liquid pump or controller.

As indicated above, the length of tubing 90 that is coated by the catheter tip coating assembly 30 is adjustable by varying the depth by which plunger tip 36 mounts to the plunger core 34. For example, with reference to FIGS. 7A and 7B, the depth 96 is defined as the distance between the cavity 40 at the interior end of plunger tip 36 and the stop tip 68 of the switch actuator 64. FIG. 7A illustrate a first, relatively small wetted depth 96-1, such as a depth of 0.125 inches, associated with the plunger core 34. The user can adjust the depth 96-1 by positioning the adjustable coupling between the plunger tip 36 and the plunger core 34. For example, a user can adjust the location and length of the threading between the plunger tip 36 and the plunger core 34, as indicated in FIG. 7B. For example, rotation of the plunger tip 36 in a counterclockwise direction relative to the plunger core 34 adjusts the relative positioning of the threads of the plunger tip 36 and the plunger core 34 and increases the depth 96-2 between the cavity 40 and the stop tip 68, such as to a depth of 0.250 inches.

As indicated above, the catheter tip coating assembly 30 is configured to wet an outer area 94 of the catheter tip. An alternative or additional usage of the assembly 30 is to have it coat the inside of the tubing 90 instead of, or at the same time as, the outside area 94 of the tubing 90. To accomplish this, the tube 50 can be manufactured from a substantially nonporous material, rather than a substantially porous material and plunger tip 36 can be manufactured from a substantially porous material, rather than a substantially nonporous material.

FIGS. 8 and 9 illustrate an arrangement of a fluid application system 200. For example, the system 200 includes a controller 202 disposed in electrical communication with a motor apparatus 204, such as a stepper motor, via an electronic control tether 203. The controller 202 and motor apparatus 204 are configured to control an amount of fluid provided to the catheter tip coating assembly 10.

The controller 202 can be configured in a variety of ways. In one arrangement, the controller 202 is configured as a motor drive card, such as a stepper motor drive card. In such an arrangement, the controller 202 includes a processor configured to generate a signal to control the motor apparatus. In another arrangement, the controller 202 is configured as a controller assembly, such as a SMARTDISPENSER dispensing unit (Fishman Corporation, Hopkinton, Mass.), which includes a memory and processor as well as a monitor 205, such as a touch screen display. In one arrangement, the monitor 205 is configured to displays a graphical user interface (GUI) that provides the user with the ability to adjust various operating parameters of the controller. For example, the GUI can be configured as a menu system with digital parameter input control and the touchscreen display can allow a user to interact with the GUI to control and adjust digital input values of associated with operation of the system 200. When combined with the functionality of the metering cylinder 208, described below, the controller 202 provides exact duplication of fluid application amounts from one system 200 to the next.

The catheter tip coating assembly 10 is selectively disposed in fluid communication with a fluid reservoir 206 and with a metering cylinder 208 via a stopcock assembly 210. The fluid reservoir 206, in one arrangement, is a container of fluid, such as an adhesive, maintained at a pressure greater than atmospheric pressure. As will be described in detail below, the fluid reservoir 206 is configured to deliver fluid to the stopcock assembly 210 and to the metering cylinder 208.

The metering cylinder 208 includes a piston (not shown) disposed within a metering cylinder housing 212 and operatively coupled to the motor apparatus 204 via a shaft, such as a lead screw. During operation, in response to control signals received from the controller 202, the motor apparatus 204 advances the plunger within the metering cylinder housing 212 to deliver fluid contained within the metering cylinder housing 212, through the stopcock assembly 210, and into the catheter tip coating assembly 10.

FIGS. 10A through 10C illustrate an arrangement of the stopcock assembly 210 having a housing 211, a first port 220 configured to be coupled to the fluid reservoir 206 via a fluid delivery line 222 as illustrated in FIGS. 8 and 9, a second port 224 configured to be coupled to the metering cylinder 208, and a third port 226 configured to be coupled to the catheter tip coating assembly 10. The first, second, and third ports 220, 224, 226 can be configured with a variety of coupling mechanisms to secure the ports to their respective receptacles. For example, in one arrangement, a connection portion 221 of the first port 220 is configured to be inserted within the lumen of the fluid delivery line 222, such as PVC tubing, and to create a friction fit with the fluid delivery line. In one arrangement, a connection portion 225 of the second port 224 is configured as a luer lock to secure the stopcock assembly 210 to the metering cylinder 208 illustrated in FIG. 8. In one arrangement, a connection portion 227 of the third port 226 is configured as a set of threads that engage and secure to mating threads of the catheter tip coating assembly 10.

The stopcock assembly 210 also includes a stopcock barrel 228 carried by the housing 211 and configured to selectively couple the first port 220 to the second port 224 and the second port 224 to the third port 226. For example, the stopcock barrel 228 defines a fluid pathway 236 that allows flow of the fluid between the first port 220 and the second port 224 when the stopcock barrel 228 is disposed in a first position, as shown in FIG. 11, and between the second port 224 and the third port 226 when positioned in a second position, as shown in FIG. 12.

The stopcock assembly 210 also includes a set of bleed valves 230, 232 disposed in fluid communication with an internal volume 234 of the stopcock assembly 210. The bleed valves 230, 232 are configured to be positioned between a closed position, such as illustrated in FIG. 10B and an open position, such as illustrated in FIG. 10A. In the closed position, the bleed valves 230, 232 seal the internal volume 234 of the stopcock assembly 210 from the atmosphere. In the open position, the bleed valves 230, 232 expose the internal volume 234 of the stopcock assembly 210 to the atmosphere.

The fluid dispensing system 200 is configured to allow a user to fill an empty metering cylinder 208 while minimizing any disassembly and reassembly of the system 200.

Prior to beginning a filling procedure, the metering cylinder 208 in disposed in a substantially emptied state. For example, the plunger of the metering cylinder 208 can be disposed in proximity to the stopcock assembly 210 such that the volume of fluid carried by the metering cylinder 208 is less than the capacity of the metering cylinder 208.

During a filling procedure, for example, a user first opens the bleed valves 230, 232 (FIGS. 10A and 10B) on the stopcock assembly 210 to expose the internal volume 234 of the stopcock to the atmosphere. This equalizes the pressure within the stopcock assembly 210 with atmospheric pressure. The user then positions the stopcock barrel 228 in the first position, shown in FIG. 11, to dispose the fluid pathway 236 in fluid communication with the fluid reservoir 206. As indicated above, the fluid reservoir 206 is maintained under a pressure that is greater than atmospheric. Accordingly, with the stopcock barrel 227 disposed in the first position, fluid (e.g. adhesive fluid) flows from the fluid reservoir 206 to the internal volume 234 of the stopcock assembly 210. Additionally, with the bleed valves 230, 232 open to the atmosphere, the fluid flows from the internal volume 234 and into the bleed valves 230, 234 to force air contained within the internal volume 234 of the stopcock assembly 210 to the atmosphere. Once the bleed valves 230, 234 are full of fluid, the user closes the bleed valves 230, 234. The bleed valves 230, 234, therefore, allow the user to prime the stopcock assembly 210 with fluid from fluid reservoir 206 to minimize the presence of air in the system 200. Returning to FIGS. 10A and 10B, with the stopcock barrel 228 in the first position, the user then retracts the plunger of the metering cylinder 208, such as by reversing operation of the motor apparatus 204. This motion of the plunger draws fluid from the stopcock assembly 210 into the metering cylinder 208 via the second port 224, thereby filling the metering cylinder 208.

Next, during operation, the user positions the stopcock barrel 228 in the second position within the stopcock assembly housing, as illustrated in FIG. 12. With such positioning, the stopcock barrel 228 blocks the first port 220 and allows the fluid contained within the metering cylinder 208 and the stopcock assembly 210 to be delivered to the catheter tip coating assembly 10 for dispensing to a catheter tip.

In one arrangement, and with reference to FIGS. 1, 2A, and 2B, the user can remove air from the catheter tip coating assembly 10 using a bleed valve 60. For example, to vent air trapped inside the reservoir 20 the user opens the bleed valve 60 to equalize the pressure within the housing 12 with atmospheric pressure. With such positioning, fluid flows from the reservoir 20 of the housing 12 and into the bleed valve 60 to force air contained within the reservoir 20 to the atmosphere. Once the bleed valve 60 is full of fluid, the user closes the bleed valve 60. While the bleed valve can be configured in a variety of ways, in one arrangement, the bleed valve 60 is configured as a thumbscrew that matably couples to a threaded opening defined by the housing 12.

During operation, the controller 202 and motor apparatus 204 advances the plunger within the metering cylinder 208 to dispense fluid to the catheter tip coating assembly 10, as described above. In one arrangement, the controller 202 is configured to detect a fluid volume within the metering cylinder 208. When the volume of fluid in the metering cylinder 208 reaches a low-level threshold, as detected by the controller 202, the controller 202 is configured to provide an alert signal to the user. In one arrangement, such as when the controller 202 is configured as a controller assembly (e.g., a SMARTDISPENSER dispensing unit), the alert signal is a visual alert displayed by the monitor 205. For example, with reference to FIG. 8, the controller 208 can display a pop-up message stating "Syringe empty. Hit Ok to retract." The user can then touch "Ok" on the screen 305 to cause the controller 202 to activate the motor apparatus 204 to retract the lead screw. In another example, the GUI 207 can display a graphic image of the metering cylinder showing the fluid level in the cylinder 208. Alternately, the alert signal can be configured as an auditory alert or a flashing of a light, such as a light emitting diode (LED). In response to the alert, the user stops the motor apparatus 204 and position the stopcock barrel 228 from the second position as shown in FIG. 12 to the first position as shown FIG. 10 and restarts the filling procedure as outlined above. In one arrangement, when the controller is configured as a motor drive card, the alert signal is a visual alert provided by the metering cylinder 208. For example, the metering cylinder 208 can be configured with a window that allows a user to visualize the amount of fluid contained therein.

In one arrangement, with reference to FIG. 9, the metering cylinder 208 includes a sleeve 250 disposed about the syringe of the metering cylinder 208. The sleeve, such as an aluminum sleeve, is configured to couple the stopcock assembly 210 to the motor apparatus 204 and to minimize motion or wobble of the stopcock assembly 210 relative to the motor apparatus 204. The sleeve 250 can be configured with a visual indicator to provide a user with notification regarding the amount of fluid within the metering cylinder 208. For example, the sleeve 250 can define a window that allows the user to view the position of the plunger within the metering cylinder 208 in order to determine when the appropriate time is to refill the metering cylinder 208.

As indicated above, the user manually operates stopcock barrel 228 during a filling procedure. Such description is by way of example only. In one arrangement, the system 200 includes a detection system that automatically positions the stopcock barrel 228 to engage the filling procedure in response to detecting a low level of fluid in the metering cylinder 208. For example, the system 200 can include a sensor disposed in electrical communication with a controller, such as a processor and memory. The sensor is configured to detect an amount of fluid present within the metering cylinder 208 and provides a signal to the controller. Upon receipt, the controller compares the signal to a threshold value. In one arrangement, when the signal value falls below the threshold value, the controller causes a motor disposed in operational communication to position the stopcock barrel 228 from the second position as shown in FIG. 12 to the first position as shown in FIG. 11. The controller can then cause the motor apparatus 204 to fill the metering cylinder 208, as described above, and to cause the motor to position the stopcock barrel 228 from the first position as shown in FIG. 11 to the second position as shown in FIG. 12.

In one arrangement, the catheter tip coating assembly 10 includes a notification mechanism to indicate the completion of a tube coating cycle. For example, the catheter tip coating assembly 10 includes a light (not shown), such as an LED, that becomes activated (illuminates) when the motor 204 energizes and that becomes deactivated when the motor de-energizes.

FIG. 13 illustrates a sectional view of an arrangement of the plunger tip 36 of the catheter tip coating assembly 10. As illustrated, the plunger tip 36 defines a receptacle or cup 260 at the base 262 of the catheter support pin 264 such that the pin 264 defines a hood element that substantially extends over and covers seam formed between tubing 90 and the stem shoulder 262. As a user disposes a tubing 90 onto the support pin 264 and positions the end 92 of the tubing 90 against the base 262, the receptacle 260 captures the end 92 of the tubing 90 to seal the end 32 against the plunger tip 36. The configuration of the receptacle 260 minimizes leakage of the fluid or adhesive applied to the tubing 90 to either inside or outside of the catheter lumen 266, depending upon the location of the fluid application.

While various embodiments of the innovation have been particularly shown and described, it will be understood by those skilled in the art that various changes in form and details may be made therein without departing from the spirit and scope of the innovation as defined by the appended claims.

For example, with respect to FIGS. 6A and 6B, the dispensing system 10 includes a luer fitting 21 configured to be coupled to a fluid source (not shown) or to a stopcock assembly 210. As indicated, the luer fitting 21 is coupled to the second end cap 18 and delivers fluid from the luer fitting 21 along a longitudinal axis of the dispensing system 10, past the spring 54, and into the reservoir 20. Such indication is by way of example only. In one arrangement, as illustrated in FIGS. 14 and 15, the stopcock assembly 210 couples to the housing 12 of the dispensing system 10 and is configured to deliver fluid into the reservoir 304 along a transverse axis 282 of the dispensing system 10.

For example, as best illustrated in FIG. 14, the reservoir 304 is defined as the volume disposed between the plunger 32, an inner surface of the housing 12, and a stopper 300, such as an O-ring, disposed between the plunger 32 and the inner surface of the housing 12. In use, as the stopcock assembly 210 delivers fluid into the reservoir 304, the stopper 300 minimizes fluid flow from the reservoir 304 to a chamber 302 that contains the spring 54. Such a configuration allows the spring 54 to contract and expand within the substantially fluid-free environment substantially free of damping effects caused by the fluid on the operation of the spring 54. Additionally, the configuration of the stopper 300, the plunger 32, and the inner surface of the housing 12 limits the volume of fluid contained by the reservoir 304. For example the volume of the reservoir 304 can be about 0.25 cubic centimeters.

What is claimed is:

1. A catheter tip coating assembly, comprising:
   a housing defining a fluid reservoir and having a fluid outlet configured to dispense fluid to an end of a piece of tubing; and
   a valve assembly carried by the housing and disposed in fluid communication with the fluid reservoir, the valve assembly configured to receive the piece of tubing and configured to move between a first position to limit fluid communication between the fluid reservoir and the fluid outlet and a second position to provide fluid communication between the fluid reservoir and the fluid outlet to dispense fluid to the end of the piece of tubing, wherein the fluid outlet is configured as a porous tube disposed between the fluid reservoir and at least a portion of the valve assembly, the valve assembly including:
   a plunger tip having a shaft portion configured to receive the end of the piece of tubing and selectively position the end of the piece of tubing within a bore defined by the porous tube;
   a plunger core having a first end coupled to the plunger tip, the plunger core selectively disposed within the bore defined by the porous tube; and
   a plunger coupled to a second end of the plunger core, the plunger selectively disposed about an outer diameter of porous tube.

2. The catheter tip coating assembly of claim 1, wherein the valve assembly is further configured to move between the second position to provide fluid communication between the fluid reservoir and the fluid outlet and the first position to limit fluid communication between the fluid reservoir and the fluid outlet.

3. The catheter tip coating assembly of claim 1, wherein:
in the first position, the plunger is disposed about the outer diameter of the porous tube to limit fluid communication between the fluid reservoir and the porous tube, the plunger core is disposed within the bore defined by the porous tube to limit fluid communication between the porous tube and the end of the piece of tubing, and the plunger tip is configured to maintain the end of the piece of tubing external to the porous tube; and
in the second position, the plunger is at least partially disposed about the outer diameter of the porous tube to provide fluid communication between the fluid reservoir and the outer diameter of the porous tube, the plunger core is at least partially disposed external to the bore defined by the porous tube to provide fluid communication between the porous tube and the end of the piece of tubing, and the plunger tip is configured to maintain the end of the piece of tubing within the bore defined by the porous tube.

4. The catheter tip coating assembly of claim 1, wherein the plunger tip and the first end of the plunger core comprises an adjustable coupling disposed there between, the adjustable coupling configured to adjust a length of the end of the piece of tubing disposed within the bore defined by the porous tube.

5. The catheter tip coating assembly of claim 4, wherein the plunger tip defines a first set of threads and the plunger core defines a second set of threads, relative positioning of the first set of threads and the second set of threads configured to adjust the length of the end of the piece of tubing disposed with in the bore defined by the porous tube.

6. The catheter tip coating assembly of claim 1, wherein:
the plunger comprises a set of ribs disposed about an outer periphery of the plunger; and
an inner wall of the housing defines a set of channels corresponding to the set of ribs, the set of ribs slidably disposed within the corresponding set of channels.

7. The catheter tip coating assembly of claim 1, further comprising a switch carried in the housing, the switch configured to generate a signal in response to the valve assembly moving between the first position and the second position.

8. The catheter tip coating assembly of claim 7, wherein the switch comprises:
a set of switch contacts carried by the housing; and
a switch actuator configured to selectively contact the set of switch contacts to generate the signal in response to the valve assembly moving between the first position and the second position.

9. The catheter tip coating assembly of claim 1, further comprising a bleed valve disposed in fluid communication with the fluid reservoir defined by the housing.

10. The catheter tip coating assembly of claim 1, wherein the plunger tip comprises a shoulder element and defines a receptacle for the end of the piece of tubing, relative to the shoulder element, the receptacle having a hood element configured to substantially extend over a seam formed between the end of the piece of tubing and the shoulder element.

11. A fluid application system, comprising:
a catheter tip coating assembly comprising:
a first housing defining a first fluid reservoir and having a fluid outlet configured to dispense fluid to an end of a piece of tubing, and
a valve assembly carried by the first housing and disposed in fluid communication with the first fluid reservoir, the valve assembly configured to receive the piece of tubing and configured to move between a first position to limit fluid communication between the first fluid reservoir and the fluid outlet and a second position to provide fluid communication between the first fluid reservoir and the fluid outlet to dispense fluid to the end of the piece of tubing;
a metering cylinder disposed in fluid communication with the first fluid reservoir of the catheter tip coating assembly and disposed in operational communication with a motor apparatus;
a controller disposed in electrical communication with the motor apparatus and configured to control an amount of fluid provided to the catheter tip coating assembly from the metering cylinder; and
a stopcock assembly configured to selectively couple a second fluid reservoir with the catheter tip coating assembly and with the metering cylinder.

12. The fluid application system of claim 11, wherein the stopcock assembly comprises:
a second housing;
a first port coupled to the second housing and disposed in fluid communication with the second fluid reservoir;
a second port coupled to the second housing and disposed in fluid communication with the metering cylinder;
a third port coupled to the second housing and disposed in fluid communication with the catheter tip coating assembly; and
a stopcock barrel carried by the housing, the stopcock barrel configured to selectively couple the first port to the second port and couple the third port to the second port.

13. The fluid application system of claim 12, wherein the stopcock assembly comprises a set of bleed valves coupled to the second housing and disposed in fluid communication with an internal volume defined by the second housing, the set of bleed valves configured to be disposed between a first position to seal the internal volume from the atmosphere and a second position the expose the internal volume to the atmosphere.

14. The fluid application system of claim 11, wherein the controller is configured to:
detect a fluid volume contained by the metering cylinder; and
in response to detecting a low-level threshold of the fluid volume contained by the metering cylinder, generate an alert signal.

15. The fluid application system of claim 11, wherein the controller comprises a monitor configured to display a control menu and to receive digital parameter input control based upon input from the control menu.

16. The fluid application system of claim 11, wherein the metering cylinder comprises a sleeve that couples the stopcock assembly to the motor apparatus.

17. The fluid application system of claim 11, wherein a plunger tip and a first end of a plunger core comprises an adjustable coupling disposed there between, the adjustable coupling configured to adjust a length of the end of the piece of tubing disposed within a bore defined by a porous tube.

18. The fluid application system of claim 11, wherein a plunger tip comprises a shoulder element and defines a receptacle for the end of the piece of tubing, relative to the shoulder element, the receptacle having a hood element configured to substantially extend over a seam formed between the end of the piece of tubing and the shoulder element.

* * * * *